(12) United States Patent
Turner

(10) Patent No.: US 7,584,850 B2
(45) Date of Patent: Sep. 8, 2009

(54) CHILDREN'S FIRST AID KIT FOR CUTS AND SCRAPES

(76) Inventor: James W. Turner, 434 Spring Trail, Warrior, AL (US) 35180

( * ) Notice: Subject to any disclaimer, the term of this patent is extended or adjusted under 35 U.S.C. 154(b) by 313 days.

(21) Appl. No.: 11/534,626

(22) Filed: Sep. 22, 2006

(65) Prior Publication Data
US 2007/0292344 A1 Dec. 20, 2007

Related U.S. Application Data

(60) Provisional application No. 60/801,422, filed on May 19, 2006.

(51) Int. Cl.
*B65D 69/00* (2006.01)
*B65D 71/00* (2006.01)
*B67D 1/07* (2006.01)
(52) U.S. Cl. .................. 206/570; 206/229; 206/803; 222/192
(58) Field of Classification Search ............ 206/570, 206/210, 229, 438, 440, 803, 822; 222/192, 222/320, 321.1, 321.7–321.9, 394, 399, 402.1, 222/383.1, 383.3, 385; 239/337, 329, 333
See application file for complete search history.

(56) References Cited

U.S. PATENT DOCUMENTS 2,135,238 A * 11/1938 Malik ......................... 206/480
2,354,402 A * 7/1944 Petruccione et al. ......... 206/225
2,740,516 A * 4/1956 Renn ........................... 206/229
3,292,993 A * 12/1966 Musso ......................... 422/300
4,598,664 A * 7/1986 Hamlin ....................... 118/325
6,132,691 A * 10/2000 Coles .......................... 422/300
6,186,349 B1 * 2/2001 Tempongko ............... 220/4.22
6,439,379 B2 * 8/2002 Taormina ....................... 206/5
7,104,468 B2 * 9/2006 Stengel ....................... 239/302
7,143,958 B1 * 12/2006 Dorney ....................... 239/289
7,370,754 B2 * 5/2008 Kushner ....................... 206/38
2006/0283739 A1 * 12/2006 Wang .......................... 206/379
2007/0221515 A1 * 9/2007 Lindley ....................... 206/223
2007/0254854 A1 * 11/2007 Magallon et al. ............ 514/150

FOREIGN PATENT DOCUMENTS

CA 2541447 A1 * 3/2008
GB 2284862 A * 6/1995
GB 2350604 A * 6/2000

* cited by examiner

*Primary Examiner*—Mickey Yu
*Assistant Examiner*—Melissa L Lalli
(74) *Attorney, Agent, or Firm*—West & Associates, A PC; Charlotte Rodeen-Dickert; Stuart J. West

(57) ABSTRACT

The present disclosure provides a children's first aid kit suitable for treating minor scrapes and cuts. The compact kit is integral with a reusable cooling mechanism designed to provide a cooling sensation to the injured area. The kit is further integral with a supply of antiseptic medicine and bandages, and can be easily carried and made available in any situation. An optional applicator to dye the skin surrounding the wound to create a temporary design can be supplied.

16 Claims, 4 Drawing Sheets

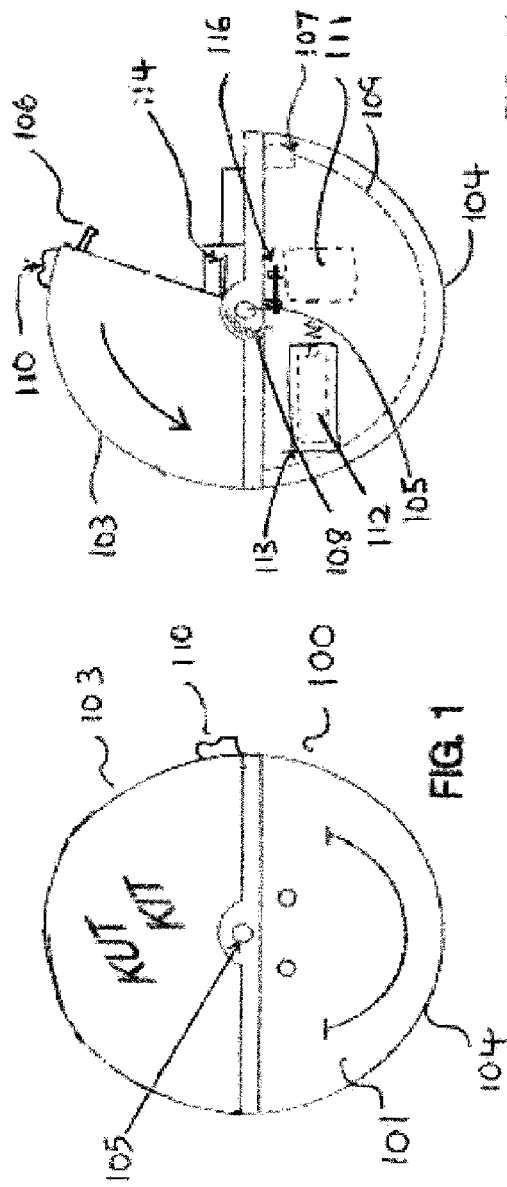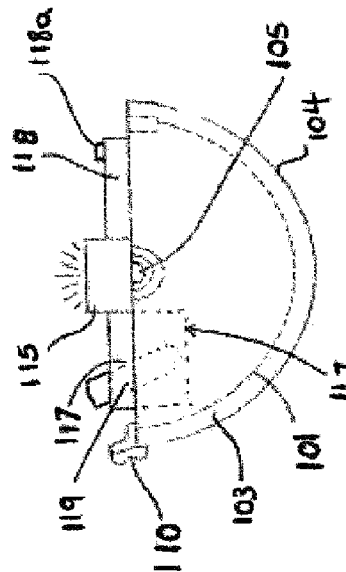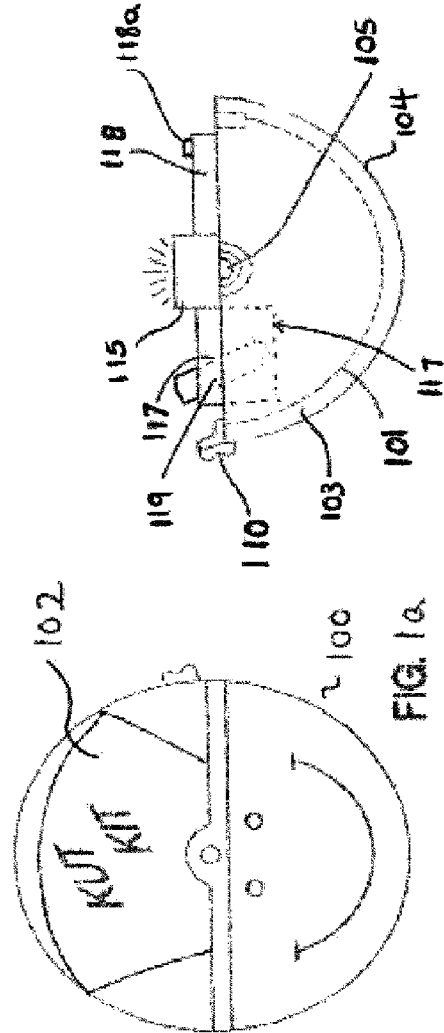

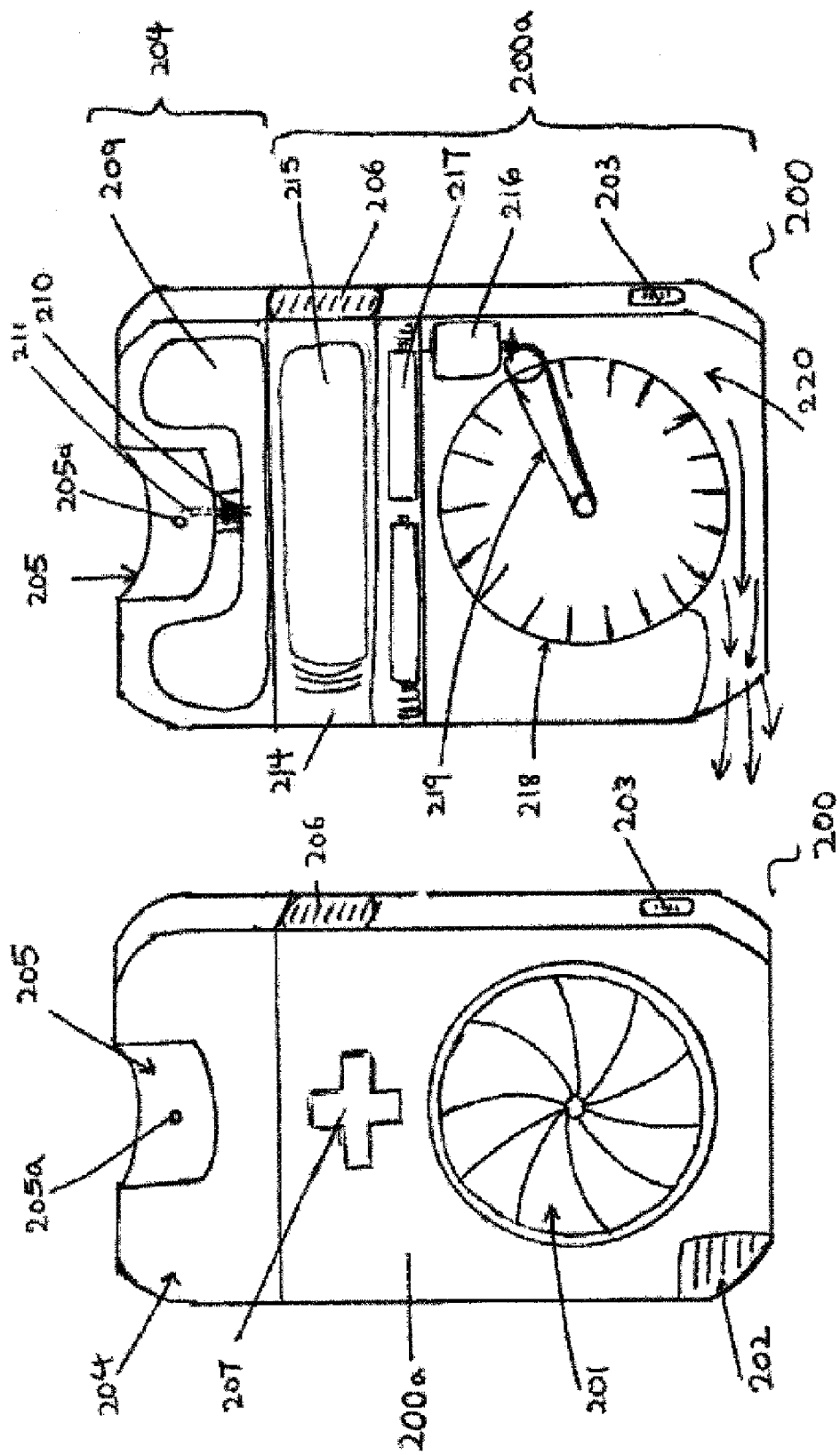

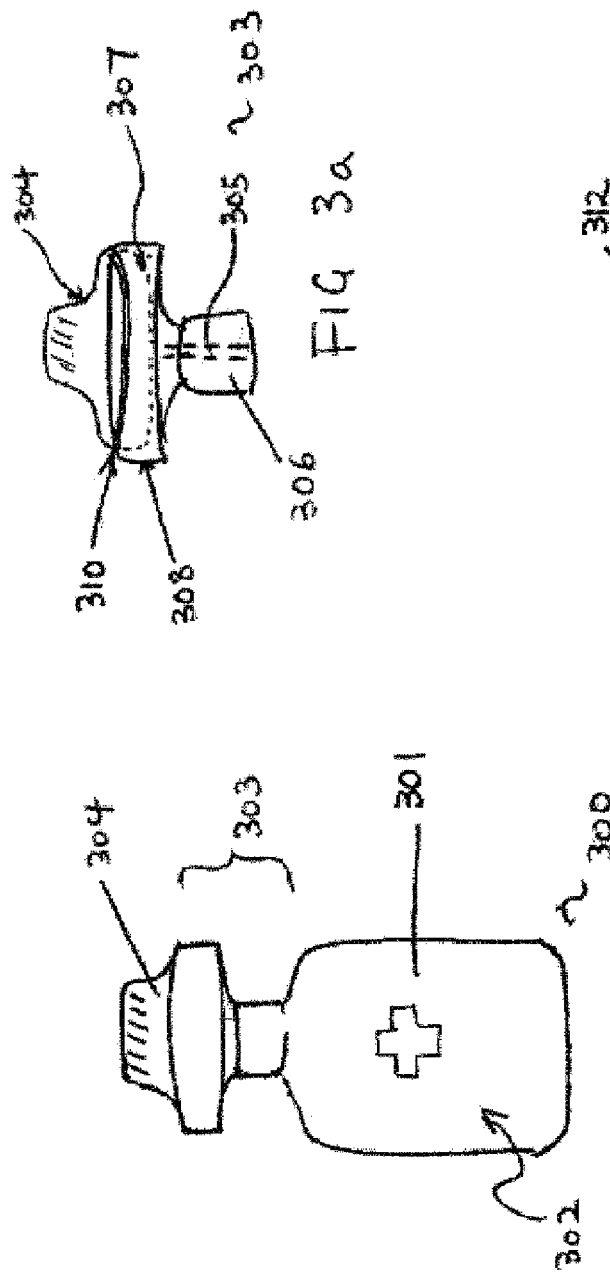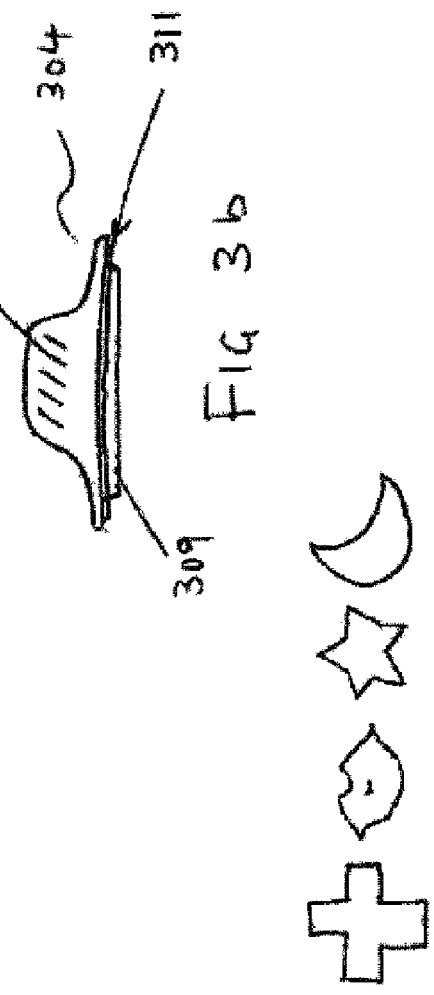

CHILDREN'S FIRST AID KIT FOR CUTS AND SCRAPES

CLAIM OF PRIORITY

This application claims priority to U.S. Provisional Application 60/801,422 filed May 19, 2006.

FIELD OF THE INVENTION

The current disclosure relates to children's first aid kits to treat minor cuts and scrapes.

BACKGROUND

Young children are, by nature, accident prone. Bumps and bruises, cuts and scrapes go hand in hand with their everyday adventures. From falling down while running, walking into things and getting cuts and bruises, no one gets through childhood without some sort of mishap.

Along with being accident prone, children usually have a fairly low tolerance for pain. "Crybabies" would run to their caretakers when confronted with a minor cut, in dire need for comfort from an adult to take their mind off the discomfort. This can be exasperated by the stinging sensation on the open wound caused by disinfectants or antiseptics used to treat the injury. The adult guardian is often requested to "make it better" right away. This usually involves the time-honored tradition of blowing on the wound. The air creates a cooling, soothing sensation that can alleviate some feeling of pain. However, blowing on the open wound can greatly increase the risk of infection from germs and bacteria from the mouth, thereby prolonging the time the wound would cure or even worsen the injury. The caretaker blowing on the wound may also reach a state of hyperventilation as the child screams for further relief.

Another way to apply cooling to the injured area is to use vinyl packs filled with a non-toxic silica gel, commonly known as "Cold Packs." Chattanooga Group of Hixson, Tenn., for instance, markets a cold pack in the shape of a teddy bear under the name "Boo Boo Pac" for use with children. However, cold packs need to be kept refrigerated before use and can not be readily made available when away from a refrigerator or freezer. This makes them impractical when the child is injured away from the home. Also, since these cold packs are meant to be re-useable, direct application to an open wound may not be hygienic.

Alternatively, "instant cold packs" that deliver cooling by means of an endothermic chemical reaction resulting from mixing two substances, (typically ammonium nitrate or urea with water) can be used where there is no refrigeration available. These packs can provide cooling pain relief, and help reduce swelling and inflammation, and can be used to treat sprains, cuts and bruises. However, since these instant cold packs are spent and have to be disposed after only one use, these are often impractical and unnecessarily expensive for minor cuts and scrapes in children.

What is desired, therefore, is a device that can provide cooling relief to a minor wound which is convenient and hygienic.

The device should be economical and be reusable for numerous times.

The device should contain medicines, ointments, antiseptics and/or bandages capable of treating minor cuts and scrapes in a compact unit.

The device should have a kid-friendly design, said design helping to alleviate some of their anxiety in getting treatment for their wound.

The device should allow the child to participate the tending of his or her own wound, in order to learn important first aid knowledge.

SUMMARY OF THE INVENTION

The present disclosure provides a children's first aid kit suitable for treating minor scrapes and cuts. The compact kit is integral with a reusable cooling mechanism designed to provide a cooling sensation to the injured area. The kit is further integral with a supply of antiseptic medicine and bandages, and can be easily carried and made available in any situation. An optional applicator to dye the skin surrounding the wound to create a temporary design can be supplied.

BRIEF DESCRIPTION OF THE DRAWINGS

FIG. 1 depicts a front view of an embodiment of the children's first aid kit in its closed configuration.

FIG. 1a depicts an alternate cosmetic design for the embodiment of the children's cut kit depicted in FIG. 1.

FIG. 1b depicts the embodiment of FIG. 1. as the top cover is being opened.

FIG. 1c depicts the first aid kit in depicted in FIG. 1 in its open configuration.

FIG. 2 depicts an exterior view of an alternate embodiment of the children's first aid kit.

FIG. 2a shows a cut-away interior view of the alternate embodiment of the Kit.

FIG. 3 depicts an embodiment of the optional antiseptic dye dispenser.

FIG. 3a depicts the reservoir cap according to the embodiment of the antiseptic dye dispenser.

FIG. 3b depicts the antiseptic dye applicator according to the embodiment of the antiseptic dye dispenser.

FIG. 3c depicts exemplary stamp shapes of the antiseptic dye applicator.

DETAILED DESCRIPTION

Figure 2B:
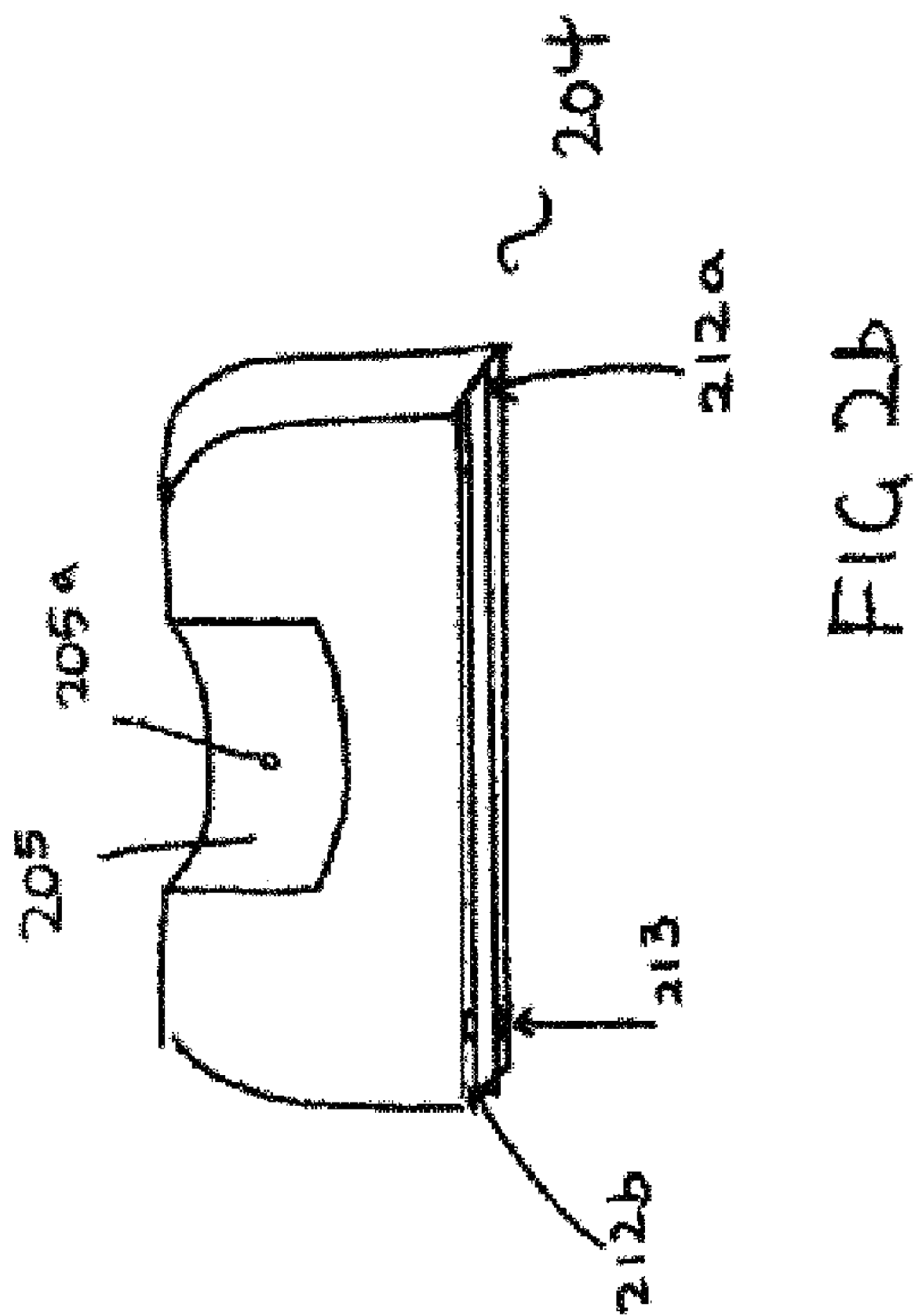
FIG. 2b shows a stand-alone replacement antiseptic container unit according to the alternate embodiment of the Kit.

FIG. 1 depicts a front planar view of one embodiment of the novel children's first aid kit 100 (hereinafter "Kut Kit" or "Kit"). In this particular embodiment, the Kut Kit has a design that looks depicts a simple design that appeals to children (in this case, a stylized "smiley face" 101). An alternate design showing a smiley face with a nurse's cap 102 is shown in FIG. 1a. These designs are meant to be illustrative only and are not meant as limiting. In general, any design that appeals to children may be used. Alternatively, a simple utilitarian design with plain colors designating a first aid kit may be used.

In one embodiment of the Kit, it has a generally circular shape, and is of a size that is compact enough to be easily carried in a pocket, purse, or the glove compartment of a car. This generally means the Kit should be a size that fits comfortably in the palm of the hand, so that it can be held and operated with ease.

Externally, the Kit is comprised of a top cover 103 and a base 104. A one-touch quick release button 105 is centrally located which, when pressed, retracts the top cover 103. In alternate embodiments of the Kit, the quick release button can be located in another convenient location on the base. The top cover 103 and base 104 should have a generally semi-circular shape; the base 104 having a slightly greater diameter than the top cover 103 such that the top cover 103 can be housed within the base 104 when the top cover 103 is retracted.

Refer to FIG. 1b. The top cover is normally held closed by means of a latch 106 and catch 107 mechanism. Depressing the release button 105 releases the latch 106 from the catch 107, allowing spring 108 to exert tension on the top cover to retract it into the base 104. The top cover 103 slides into the base 104 on a track 109 situated internally in the base 104.

FIG. 1c depicts the Kut Kit in open configuration, with the top cover 103 fully retracted inside the base 104. An external thumb/finger retractor 110 is integral with the top cover 104 on the latch side. To close the top cover 104, the thumb or finger is placed on thumb/finger retractor 110 to draw top cover 103 along track 109. The cover 103 is drawn clockwise until the latch 106 locks onto catch 107 and the cover is held closed.

Refer back to FIG. 1b. The base 104 houses internally a small DC motor 111 which is powered by at least one common dry cell-type battery 112 housed in a battery compartment 113. The battery compartment 113 should be accessible from the back of the base 104 to allow changing of batteries. The motor drives a fan 114 housed in a blower housing 115. In the embodiment of the Kit depicted in FIG. 1b, the fan 114 is mounted horizontally on a plane perpendicular to the front surface of the Kit. In alternate embodiments, a paddle wheel fan with blades mounted radially can be used.

The motor 111 can be operated by a electrical contact switch (not shown) that is integral with the top cover 103, allowing the motor 111 to turn on automatically when the cover 103 is retracted and the electrical circuit is closed. Alternatively, a conveniently placed switch on the exterior of the base may be used. When the motor 111 is turned on, it rotates the fan blades 114 to create a gust of air which is directed outward of the base through the blower assembly 115. If the fan is placed off-axis to the motor, a gear assembly 116 may be used. To facilitate the movement of air, an air intake (not shown) is located in the back or side of the base 104 for the intake of air to the blower assembly 115.

Refer to FIG 1c. When the top cover 103 is retracted, the base reveals a compartment 117 for adhesive bandages and/or antiseptic wipes 119, the blower assembly 115, and an antiseptic spray compartment 118.

The adhesive bandage compartment 117 extends partially into the base 104. The compartment 117 can be a open-top box or trough, since the compartment 117 will usually be covered by the top cover 103 when the Kit is not in use. This allows quick access to the bandages and/or antiseptic wipes 119 when the top 103 is retracted. Additionally, disposable antiseptic wipes may be stored to clean the inflicted area. In an alternate embodiment, a tension plate or a cover for the compartment may be used to secure the bandages in the compartment.

To use the Kit, an adult guardian first retrieves it from a convenient storage place. Because of the Kit's small footprint, it can be stored and made readily available in any situation. The adult depresses the quick-release button 105 to retract the top cover 103 into the base 104, revealing the blower assembly 115, antiseptic spray 118 and adhesive bandages and/or antiseptic wipes 119. First, an antiseptic wipe may be used to clean the inflicted area. Next the antiseptic spray is applied to the inflicted area. The blower can then be activated to provide a hygienic cooling breeze to the wound to alleviate the stinging sensation of the antiseptic. When the stinging sensation is gone, an adhesive bandage can be applied.

FIG. 2 depicts an alternate embodiment of the Kut Kit 200. In this embodiment, the Kit takes on a generally rectangular shape, but has the same general features in the embodiment described above. FIG. 2 depicts an exterior view of the Kit according to this embodiment. The Kit is comprised of a top portion and a base unit 200a. The top portion comprises a self-contained removable antiseptic spray container unit 204 with finger depress antiseptic spray button 205 and antiseptic spray nozzle 205a. The base unit 200a comprises an air intake grill 201, a blower air exhaust 202, an on/off switch for the blower 203, and a sliding panel 206 for access to stored adhesive bandages and/or antiseptic wipes. A "Red Cross" symbol 207 is featured on the front. FIG. 2b depicts a stand-alone antiseptic spray container unit 204 unattached from the base unit.

FIG. 2a shows a cut-away interior view of the rectangular embodiment of the Kit. As in the embodiment of the Kit discussed previously, the antiseptic spray can be stored under pressure in a pressurized cartridge 209, or alternatively be stored in a simple un-pressurized container and dispensed with a pump spray. In either case, the self-contained antiseptic spray container 204 should be sanitary and resistant to breakage, and is disposable when the antiseptic runs dry (i.e., the entire container unit 204 is replaced with a fresh one, not refilled). Finger depress button 205 rides on a spring 210 which asserts force to return the button 205 to its original (un-pressed) position. A tube 211 runs from the antiseptic container 209 to the antiseptic spray nozzle 205, and the antiseptic is dispensed in a spray through the nozzle 205 when the finger depress button 205 is depressed.

Optionally, the finger depress button can have child-proof features such as a child-proof lock. A preferred method would be to lift the finger press button and to turn it 180 degrees and then press down to disable the button from being depressed and dispensing antiseptic. Alternatively, any child-proofing method convenient or known may be used.

FIG. 2b shows a replacement antiseptic container unit 204 without being attached to the base unit 200a of the Kit. At the bottom are tracks 212a, 212b that run parallel to the length of the container unit 204. Track locks 213 are present near one end of the tracks. Matching grooves and corresponding breaks (not shown) for locking the track locks 213 are located on the top of the base unit 200a. To replace a spent antiseptic container unit 204, the unit is slid sideways along the grooves on top of the base unit 200a until the unit disengages from the base. Slight force is needed to disengage the track locks 213 from the corresponding breaks on the base unit 200a. A fresh antiseptic container unit 204 can then be installed by matching the tracks 212a, 212b with the corresponding grooves on base unit 200a, and sliding the unit 204 towards the distal end until the track locks 213 engage with the corresponding breaks. In alternate embodiments of the Kit, any method convenient or known can be used to engage the antiseptic container unit with the base unit.

Refer back to FIG. 2a. The base unit 200a has an adhesive bandage and/or antiseptic wipe storage compartment 214 for storing a supply of bandages and/or wipes 215. The bandages can be accessed through sliding panel 206. In alternate embodiments, any means convenient or known for closing the storage compartment 214 can be used.

The base unit 200a further comprises a motorized blower unit. A motor 216 is powered by common dry cell type batteries 217 and is turned on and off by switch 203. The motor drives a paddle wheel fan 218 through a conventional gear or belt assembly 219. When rotating, the paddle wheel fan 218 moves the air (which is intake through air intake grill 201 on the exterior of base unit 200a) thorough air duct 220 and is directed out blower air exhaust 202. In alternate embodiments of the Kit, rotary fan blades may be used to direct the air flow.

This alternate embodiment of the Kit is used in a similar manner as the first embodiment disclosed above, and comprises the steps of cleaning the wound, applying the antiseptic spray, cooling the wound by using the blower, then dressing the wound in the supplied adhesive bandage.

In a further embodiment of the Kit, an optional dispenser of antiseptic dye is included. FIG. 3 depicts an embodiment of the antiseptic dye dispenser 300. In this embodiment, the dispenser 300 comprises a small squeeze bottle 301 containing an antiseptic dye 302, an antiseptic reservoir cap 303, and an antiseptic applicator cap 304. An antiseptic dye approved for the treatment and dyeing of minor cuts and scrapes that is known or convenient to practitioners skilled in the art may be used to temporarily apply coloring and/or a temporary "tattoo" to the skin surrounding the wounded area.

FIG. 3a depicts a cross-sectional view of the reservoir cap 303. To dispense the antiseptic dye onto the antiseptic applicator cap 304, the squeeze bottle 301 is lightly squeezed to pump the antiseptic dye 302 from the squeeze bottle 301 up through a small capillary tube 305 in the neck of the reservoir cap 306. The capillary tube 305 draws the antiseptic dye to fill an antiseptic dye reservoir 307 which is situated interior to the cap receptor 308 for the antiseptic applicator cap 304. The bottom of the applicator cap is integral with a hygienic foam or sponge applicator 309 which absorbs an amount of the antiseptic dye when the applicator 309 is immersed in the antiseptic dye reservoir 307. The applicator 309 is immersed in the reservoir when the applicator cap 304 is screwed closed onto the cap receptor 308. The cap receptor 308 has screw threads (female) 310 to receive the screw threads (male) 311 of the antiseptic applicator cap (shown in FIG. 3b) so that the cap can be closed tightly to form a leak-proof seal with the cap receptor.

Once the sponge applicator 309 has absorbed the antiseptic dye, the applicator cap 304 is twisted off the cap receptor 308. The applicator cap 304 has a finger grip with threads 312 on top to allow easy twisting of the cap. The sponge applicator 309 is a stamp with a flat surface that can take a variety of shapes. Exemplary shapes are depicted in FIG. 3c. These shapes are meant as examples only and are not meant to be limiting. The wet sponge applicator 309 is applied to the wounded area in a stamping motion, and the dye will leave a temporary "tattoo", or colored design, on the skin. The "tattoo" serves to hide the wound and the cheerful design and colors will keep the child's mind off the injury.

In further embodiments of the Kit, the applicator sponge is saturated with a dry dyeing agent that is activated when the sponge applicator absorbs a clear antiseptic liquid. This antiseptic liquid may be stored in the same manner as in the embodiments discussed in the embodiments discussed in FIGS. 1 and 2, infra. To activate the dye, the antiseptic can be sprayed onto the applicator sponge first, in the same manner as spraying the antiseptic directly on the wound as discussed above.

The Kit, in all the embodiments discussed herein, creates a calming, soothing, even fun, experience for the injured child. It should help to calm even the most hysteric, distracted child, allowing the child to participate in the first aid application. This can help them learn important first aid skills that would not be possible if they were distraught with the injury.

Although the invention has been described in conjunction with specific embodiments thereof, it is evident that many alternatives, modifications and variations will be apparent to those skilled in the art. Accordingly, the apparatus as described and hereinafter claimed is intended to embrace all such alternatives, modifications and variations that fall within the spirit and broad scope of the appended claims.

What I claim is:

1. A first aid kit for children comprising:
   a compact carrying case having a generally rectangular exterior,
   said generally rectangular exterior comprising a top portion and a bottom portion which can be separated,
   said compact carrying case housing an antiseptic spray dispenser, a motorized air blower, a plurality of individually packaged first aid medicines,
   wherein said top portion is a disposable antiseptic spray dispenser,
   said bottom portion being integral with said motorized air blower, and
   a storage compartment for said plurality of individually packaged first aid medicines.

2. The first aid kit of claim 1, wherein said individually packaged first aid medicines is selected from the group consisting of adhesive bandages, antiseptic wipes, antiseptic creams, gauze bandages, anti-itch medicines and fever-reduction medicines.

3. The first aid kit of claim 1, wherein said antiseptic spray dispenser stores antiseptic spray under pressure and dispenses the antiseptic spray by aerosol means.

4. The first aid kit of claim 1, wherein said antiseptic spray dispenser dispenses antiseptic spray by means of a spray pump.

5. The first aid kit of claim 1, further comprising
   a bottle of antiseptic dye,
   said antiseptic dye capable of dyeing the skin for a period of time that is shorter than the time required for a minor cut to heal,
   an antiseptic dye applicator,
   said applicator capable of applying said antiseptic dye directly on the skin surface to dye the skin.

6. The first aid kit of claim 1, further comprising
   an applicator,
   said applicator being saturated with a dry dyeing agent that is activated when said applicator absorbs an antiseptic liquid,
   said applicator capable of being applied directly on the skin surface to dye the skin.

7. The first aid kit of claim 1, wherein said motorized blower comprises a plurality of rotary fan blades, an electric motor, said electric motor powered by at least one dry cell type battery, and an electrical switch to turn the motor on and off.

8. The first aid kit of claim 1, wherein said motorized blower comprises a paddle wheel fan assembly, an electric motor, said electric motor powered by at least one dry cell type battery, and an electrical switch to turn the motor on and off.

9. A first aid kit for children comprising:
   a compact carrying case having a generally round exterior,
   said case housing an antiseptic spray dispenser, a motorized air blower, and a plurality of individually packaged first aid medicines,
   said generally round exterior of said compact carrying case comprising a cover portion and a base portion,
   wherein said cover portion slides into said base portion to allow access to said antiseptic spray dispenser, motorized air blower, and plurality of individually packaged first aid medicines,
   a tension spring to hold the cover portion in an open position,
   a catch hook to hold the cover portion in a closed position, a release button for said catch hook, wherein depressing said release button releases said catch hook to move said cover portion from a closed position to an open position.

10. The first aid kit of claim 9, wherein said individually packaged first aid medicines is selected from the group consisting of adhesive bandages, antiseptic wipes, antiseptic creams, gauze bandages, anti-itch medicines and fever-reduction medicines.

11. The first aid kit of claim 9, wherein said antiseptic spray dispenser stores antiseptic spray under pressure and dispenses the antiseptic spray by aerosol means.

12. The first aid kit of claim 9, wherein said antiseptic spray dispenser dispenses antiseptic spray by means of a spray pump.

13. The first aid kit of claim 9, further comprising
a bottle of antiseptic dye,
said antiseptic dye capable of dyeing the skin for a period of time that is shorter than the time required for a minor cut to heal,
an antiseptic dye applicator,
said applicator capable of applying said antiseptic dye directly on the skin surface to dye the skin.

14. The first aid kit of claim 9, further comprising
an applicator,
said applicator being saturated with a dry dyeing agent that is activated when said applicator absorbs an antiseptic liquid,
said applicator capable of being applied directly on the skin surface to dye the skin.

15. The first aid kit of claim 9, wherein said motorized blower comprises a plurality of rotary fan blades, an electric motor, said electric motor powered by at least one dry cell type battery, and an electrical switch to turn the motor on and off.

16. The first aid kit of claim 9, wherein said motorized blower comprises a paddle wheel fan assembly, an electric motor, said electric motor powered by at least one dry cell type battery, and an electrical switch to turn the motor on and off.

* * * * *